United States Patent
Stevens et al.

(10) Patent No.: US 11,452,696 B2
(45) Date of Patent: *Sep. 27, 2022

(54) PHARMACEUTICAL PROCESSING

(71) Applicant: Drug Delivery International Ltd., Strathclyde (GB)

(72) Inventors: Howard Norman Ernest Stevens, Strathclyde (GB); Alexander Balfour Mullen, Strathclyde (GB); Vivekanand Bhardwaj, Zionsville, IN (US); Fiona Jane MacDougall, Strathclyde (GB); David Smith, Strathclyde (GB)

(73) Assignee: DRUG DELIVERY INTERNATIONAL LTD., Glasgow (GB)

( * ) Notice: Subject to any disclaimer, the term of this patent is extended or adjusted under 35 U.S.C. 154(b) by 0 days.

This patent is subject to a terminal disclaimer.

(21) Appl. No.: 15/526,901

(22) PCT Filed: Nov. 16, 2015

(86) PCT No.: PCT/GB2015/053472
§ 371 (c)(1),
(2) Date: May 15, 2017

(87) PCT Pub. No.: WO2016/075496
PCT Pub. Date: May 19, 2016

(65) Prior Publication Data
US 2018/0055773 A1  Mar. 1, 2018

(30) Foreign Application Priority Data

Nov. 14, 2014 (GB) .................................. 1420311

(51) Int. Cl.
*A61K 9/24* (2006.01)
*B01J 2/00* (2006.01)
(Continued)

(52) U.S. Cl.
CPC ............ *A61K 9/209* (2013.01); *A61K 9/2054* (2013.01); *A61K 9/2068* (2013.01); *A61K 9/288* (2013.01);
(Continued)

(58) Field of Classification Search
None
See application file for complete search history.

(56) References Cited

U.S. PATENT DOCUMENTS 4,132,753 A  1/1979 Blichare et al.
5,126,145 A  6/1992 Evenstad et al.
(Continued)

FOREIGN PATENT DOCUMENTS

EP    0074584 A2   3/1983
EP    0097523 A2   1/1984
(Continued)

OTHER PUBLICATIONS

Carter et al. 2002. The Role of Disintegrants in Solid Oral Dosage Manufacturing. 2002-2006 http://www.carterpharmaceuticalconsulting.com/articles/The-role-of-disintergrants.html. 3 pages.*
(Continued)

*Primary Examiner* — Lakshmi S Channavajjala
(74) *Attorney, Agent, or Firm* — DLA Piper LLP (US)

(57) ABSTRACT

A method for making a controlled release material, comprising the steps of: —
(a) forming granules comprising one or more wax and one or more disintegrant;
(b) spheronisation of the granules and (c) compaction of the spheronised granules of step so as to form the controlled release material. The invention also relates to a tablet and delayed and sustained release material made according to the method.

11 Claims, 1 Drawing Sheet

(51) Int. Cl.
   *A61K 9/20*    (2006.01)
   *A61K 9/28*    (2006.01)
   *A61K 31/00*   (2006.01)

(52) U.S. Cl.
   CPC ............ *A61K 9/2866* (2013.01); *A61K 31/00* (2013.01); *B01J 2/003* (2013.01)

(56) References Cited

U.S. PATENT DOCUMENTS

| | | | | |
|---|---|---|---|---|
| 5,310,558 | A * | 5/1994 | Pozzi | A61K 9/282 424/458 |
| 5,690,959 | A | 11/1997 | Palepu et al. | |
| 7,220,430 | B2 * | 5/2007 | Ishibashi | A61K 9/282 424/468 |
| 7,943,174 | B2 * | 5/2011 | Oshlack | A61K 9/1617 424/487 |
| 10,675,247 | B2 * | 6/2020 | Stevens | A61K 9/2866 |
| 2002/0071870 | A1 | 6/2002 | Sharma | |
| 2007/0129402 | A1 | 6/2007 | Ueki et al. | |
| 2017/0258731 | A1 * | 9/2017 | Stevens | A61K 9/2068 |

FOREIGN PATENT DOCUMENTS

| | | |
|---|---|---|
| EP | 0277741 A1 | 8/1988 |
| EP | 0418596 A2 | 3/1991 |
| JP | H6100601 A | 4/1994 |
| JP | 2003171277 A | 6/2003 |
| JP | 2013521332 A | 6/2013 |
| WO | 199427557 A1 | 12/1994 |
| WO | 200074656 A1 | 12/2000 |
| WO | 200132148 A1 | 5/2001 |
| WO | 2005041935 A1 | 5/2005 |
| WO | 2005065673 A1 | 7/2005 |
| WO | 2006017159 A1 | 2/2006 |
| WO | 2006035313 A1 | 4/2006 |
| WO | 2007052299 A1 | 5/2007 |
| WO | 20080050987 A1 | 5/2008 |
| WO | 2008157103 A2 | 12/2008 |
| WO | 2011/107749 A2 | 9/2011 |
| WO | 2011107750 A2 | 9/2011 |
| WO | 2011107755 A2 | 9/2011 |
| WO | 2016075497 A1 | 5/2016 |

OTHER PUBLICATIONS

Guo et al. Ion exchange resins as drug delivery carriers. Journal of Pharmaceutical Sciences, vol. 98 (11):3886-3902. Nov. 2009.*
Iloañsusi et al., The effect of wax on compaction of microcrystalline cellulose beads made by Extrusion and spheronization. (Drug Development and Industrial Pharmacy, 24(1), 37-44, 1998). (Year: 1998).*
Law et al., Use of hydrophilic polymers with microcrystalline cellulose to improve extrusion-spheronization. European Journal of Pharmaceutics and Biopharmaceutics 45 (1998) 57-65 (Year: 1998).*
PEG 8000, Molecular Biology Grade (Polyethylene Glycol 8000), pp. 1-3, https://www.promega.com/products/biochemicals-and-labware/biochemical-buffers-and-re . . . Jul. 31, 2019 (Year: 2019).*
Particle Sciences, Hot Melt Extrusion. Technical Brief , vol. 3, pp. 1-2 (Year: 2011).*
Young et al., Production of spherical pellets by a hot-melt extrusion and spheronization process. International Journal of Pharamceutics, 242, 87-92, 2002 (Year: 2002).*
Badawy et al., A study on the effect of wet granulation on microcrystalline cellulose particle structure and performance. Mar. 2006 pharmaceutical research 23:3 634-640 (Year: 2006).*
Cerea et al. A novel powder coating process for attaining taste masking and moisture protective films applied to tablets. International Journal of Pharmaceutics vol. 279, Issues 1-2, Jul. 26, 2004, pp. 127-139 (Year: 2004).*
Biswal et al .,Production variables affecting characteristics of pellets in melt pelletization with wax combination in a laboratory scale spheronizer (Acta Pharm, 59, 199-210, 2009) (Year: 2009).*
International Search Report and Written Opinion for International application No. PCT/GB2015/053472, dated Jan. 21, 2016.
International Search Report and Written Opinion for PCT/GB2015/053473 dated Dec. 21, 2015.
Kawashima et al., "Low-Substituted Hydroxypropylcellulose as a Sustained-Drug Release Matrix Base or Disintegrant Depending on Its Particle Size and Loading in Formulation" Pharmaceutical Research (1993), 10(3):351-355.
Obara, Application Studies of L-HPC and HPMCAS for Pharmaceutical Dosage Forms—Update, ExcipientFest Americas 2012, San Juan, PR, Specialty Chemicals Research Center, Shin-Etsu Chemical Co., Ltd., Niigata, Japan. https://ipecamericas.org/sites/default/files/ef12april24-hall.b%235-sakae.obara(shin-etsu).pdf.
Notice of Final rejection dated Feb. 4, 2020 for corresponding Japanese application 2017-545002.
European Examination Report, dated Apr. 1, 2021, issued in corresponding European Patent Application No. 15797174.8.

* cited by examiner

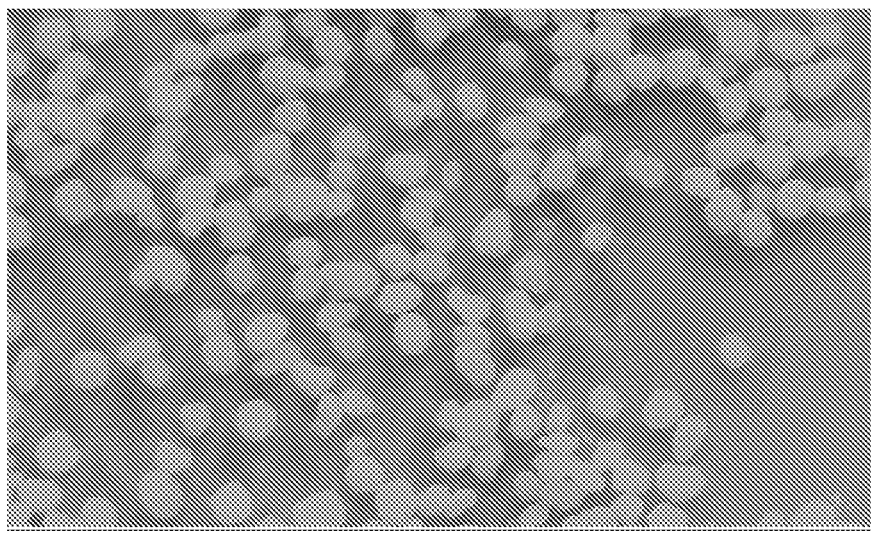

PHARMACEUTICAL PROCESSING

CROSS-REFERENCE TO RELATED APPLICATIONS

This application is a U.S. national stage filing under 35 U.S.C. § 371 of International Application No. PCT/GB2015/053472 filed Nov. 16, 2015 entitled "PHARMACEUTICAL PROCESSING", which claims the benefit of and priority to GB 1420311.1 filed Nov. 14, 2014, the disclosures of which are incorporated herein by reference in their entireties.

This invention is concerned with a method for processing wax-based granules in order to improve manufacture processing and reduce the erosion or swelling rate of said granules when used in solid oral pharmaceutical systems. The present invention describes a method of processing such granules. More particularly, the invention describes the spheronisation of melt granulated or extruded compositions comprising a wax(es) and other disintegrant(s) materials.

Methods for combining wax(es) and disintegrant materials to achieve controlled or modified release are well known in the art (see, for example, US2012/0177739A1 (Vergnault et al); WO2011107749A2 (Mullen et al)). It is generally necessary to process the powders in a manner to improve their flowability, cohesiveness and other characteristics which will enable the resulting material to be fabricated by conventional processes such as tableting into a satisfactory oral dosage form that can deliver a therapeutic agent in the desired manner.

Various processes are well-known in the pharmaceutical art for modifying starting powders or other particulate materials. In the case of wax-based dosage units, melt granulation processes are commonplace for producing particles for oral dosage forms. It is essential that such particles exhibit suitable processing properties, including, but not limited to, flow and compressibility, in order to be suitable for commercial manufacture.

It has been found that subjecting the granules of wax(es) and disintegrant to an additional spheronisation step before application as a modified or controlled (e.g. sustained or delayed) release component, resulted in improved flow properties. A surprising and unexpected additional finding is that this processing step reduces the erosion or swelling rate of tablets made from said granules when used in an oral pharmaceutical system thus resulting in further prolongation from a sustained release system, or a longer delay period when used as a delayed release barrier around a core tablet containing an API.

The art teaches away from incorporating a spheronisation step in a method for making a compacted delayed release material as spheronisation is normally considered to be used in order to produce discreet multi-particulate preparations for therapeutic applications.

Consequently, in a first aspect of the present invention, there is provided a method for making a controlled release material, comprising the steps of: —
  (a) forming granules comprising one or more wax and one or more disintegrant;
  (b) spheronisation of the granules and
  (c) compaction of the spheronised granules of step (b) so as to form the controlled release material.

Reference to the control of release achieved by the material refers to its ability to either operate as a sustained or delayed release material. A delayed release material provides a delay in the release of a therapeutic agent that may be encapsulated by a delayed release material layer in a multilayer tablet. The therapeutic agent cannot be released until the delayed release material layer has been at least partially eroded. A sustained release material includes a therapeutic agent; the therapeutic agent being liberated over a sustained period from the material as the material erodes.

The advantage of this invention is first the improvement of flow of the wax based granules following spheronisation, and so will result in enhanced processing properties. Secondly, the tablets made from granules prepared in such a manner exhibit prolonged erosion and/or swelling when used in modified or controlled release preparations and as such can provide extended delay or sustained release periods for active ingredients.

The granules of wax and disintegrant may be formed in any manner known to the skilled person that enables an acceptably homogeneous mixing of wax and disintegrant (and optionally therapeutic agent). For example, by a melt granulation technique. Such a technique involves the mixing of a disintegrant and a molten wax (and optionally therapeutic agent), whilst retaining the wax in molten form. The skilled person would be well aware when a wax is molten or not, i.e. a molten wax being in liquid form via the application of heat or energy. When in liquid form, the reduced viscosity assists the coating of particles of disintegrant and therapeutic agent.

Any method to enable the wax to remain in molten form during the step of melt-mixing can be used. For example, heat/energy may be applied to the mixture of step a. during the entire mixing step, or intermittently through the mixing step, in order to ensure that the temperature of the mixture is retained above the melting temperature of the wax. The mixture will solidify on cooling to below melting point. This may be achieved passively, e.g. by ensuring that no heat/energy source is applied to the mixture so that it returns to ambient temperature. Alternatively, heat/energy may be removed actively from the mixture, for example by applying a circulating cold water jacket around the receptacle in which the mixture is mixed. The step of mixing may continue during the cooling step in order to form granules of mixture. When granulation occurs with mixing on cooling, it has been found that a better processing is achieved when the granules are then passed through a sieve (typically 1 mm) when warm. Granulation of the mixture may therefore be simultaneous with the step of solidifying. For example, the action of stirring the mixture as it cools to a solid will granulate the mixture. Alternatively, the mixture of wax and disintegrant may be extruded and the extrudate sieved or cut/broken into granules of <1 mm.

A step of milling of the granules formed in step (a) prior to step (b) may be carried out. The granules may be milled by being passed through a sieve (e.g. a 1.25 mm or smaller) or being processed in an oscillating granulator. Milling preferably occurs whilst the mixture is warm, i.e. above room temperature.

Spheronisation is a technique known well in the art. The technique involves the rounding of amorphous or elongate particles so as to conform substantially to the shape of a sphere. This is normally achieved by friction forces being applied to the particles, optionally along with heat/energy, if required. For example, spheronisers may have a fixed side wall with a rotating bottom plate on which the particles are placed during use. Centripedal force may be applied to the granules, optionally with heat, rolling the granules against an abrasive surface in order to round and smooth each granule. Spheronisation may also be achieved in a high or low shear mixer, planetary mixer, or any other means to roll the granules and so form them into a substantially spherical shape. Spheronisation makes the granules conform substantially to the shape of a sphere (ie they become more spheroidal than their original form). This does not require the formation of perfect spheres, indeed some of the resultant spheronised granules may be acicular eg taking on a tear drop or ovoid form. The technical benefits of the current invention are thought to be achieved through more consistent coating of the disintegrant particles, thus reducing the amount of disintegrant that is exposed on the external surface. Not wishing to be restricted further, but to assist with understanding, spheronisation may occur in a heated Caleva spheroniser. The granules may be retained within an operating spheroniser for 1, 2 or 3 minutes or more, 1-5 minutes, or 3-5 minutes, and at a temperature of 60-74° C.

Waxes are organic compounds that are often insoluble in water and soluble in organic non-polar solvents. Waxes may be of plant or animal origin, or synthetic (such as those derived from petroleum). A wax is a solid at room temperature and has a melting temperature of 37 to 100° C. The wax of the present invention may be any wax capable of being eroded during transit through the gastrointestinal tract and so cannot be liquid at 37° C. The person skilled in the art is capable of determining appropriate waxes, but in the interests of clarity, suitable waxes may have a melting temperature in the range of from 37 to 100° C. For example, the wax may be carnauba wax, paraffin wax, hydrogenated castor oil, beeswax, glycerol behenate, a glycowax or any combination thereof.

The wax is provided in an amount sufficient to substantially coat the particles of disintegrant. It has been found that increasing the amount of wax in the tablet increases the time over which the erosion process takes place. For example, the wax can be provided as 20 to 80% by weight, or 30 to 70% by weight of the compressed granules.

The disintegrants of the present invention may be any compound capable of accelerating the disintegration of a tablet and/or granules of the tablet after the disintegrant comes into contact with water. The disintegrant may be an organic compound. The person skilled in the art is capable of determining appropriate disintegrants, but in the interests of clarity, suitable disintegrants may be, for example, cellulosic (for example, low-substituted hydroxypropyl cellulose, also called L-HPC). The IUPAC name for L-HPC is cellulose, 2, hydroxypropyl ether (low substituted). L-HPCs share the same CAS number with hydroxypropyl cellulose (i.e. 9004-64-2). L-HPC however differs from hydroxypropyl cellulose by the fact that it includes less hydroxypropoxy groups in the cellulose backbone. When dried at 105° C. for 1 hour, a L-HPC contains not less than 5.0% and not more than 16.0% by weight of the molecule of hydroxypropoxy groups. The disintegrant may be chosen from, but not limited to, the list of LH-11, LH-21, LH-22, LH-32, NBD-021, NBD-020, LH-B1, sodium carboxymethylcellulose, cross-linked starch, hydroxylpropylmethyl cellulose, ion exchange resins or any combination thereof.

The disintegrant is provided in an amount that can be coated substantially by the wax, but a sufficient amount to affect the disintegration of the granules of the tablet. For example, the disintegrant can be provided as 12-50% by weight of the compresssed granules of the tablet.

The controlled release material may consist only of one or more wax and one or more disintegrant. However, further pharmaceutically acceptable excipients and additives may be included. Such a form is sutiable for use as a delayed release material. One or more therapeutic agent may also be added in order to provide a sustained release of the agent from the material. Consequently, when the material is a sustained release material, it may consist of one or more wax, one or more disintegrant, one or more therapeutic agent, and optionally further pharmaceutically acceptable excipients and additives.

The controlled release material of the present invention may entirely form a tablet itself. Thus the step of compaction is to entirely form a tablet. In such a format, the material will include a therapeutic agent for its sustained release.

Alternatively, the controlled release material subjected to the processing steps of the invention may form one or more distinct portions of a tablet. For example, the controlled release material may form a core with one or more functionalised layer encapsulating the core. The core may form a tablet itself, ie forming a monolithic formulation. In such a format, the material will include a therapeutic agent for its sustained release from the core. Alternatively, the controlled release material may form a delayed or sustained release layer that encapsulates a core of a tablet (one or more functionalised layers may be provided between the core and the erodible sustained release layer).

The skilled person would be well aware how granules of the present invention may be compacted so as to form a controlled release material e.g. for a delayed release of a therapeutic agent, the therapeutic agent containing core to be encapsulated is inserted into a die and surrounded by the granulated mixture before pressure is applied so as to encapsulate the core within the compressed granulated mixture. When the granulated mixture is to form a tablet, the granulated mixture is placed into a die for a tablet or for a core of a tablet and pressure applied so as to form the shaped core or tablet.

In a second aspect of the present invention, there is provided a controlled release material made according to the methods of the first aspect of the present invention.

In a third aspect of the present invention, is provided a tablet that comprises the controlled release material made by the method of the first aspect of the present invention.

All features of the material and tablet as described in the first aspect of the present invention may equally apply to those of the second and third aspects. For example: —

The tablet may be entirely formed by the material and may optionally include a therapeutic agent mixed through the material.

Alternatively, or additionally, the tablet may include a layer that encapsulates a core of the tablet, wherein the layer is formed by the delayed release material.

The tablet or the layer formed by a controlled release material may optionally comprise a further layer, optionally this layer being the furthest removed from the core of the tablet. The further layer may comprise or consist of one or more therapeutic agent, one or more disintegrant and one or more wax. When this layer is the furthest removed from the core of the tablet, this layer may be prepared for immediate release of the therapeutic agent. The therapeutic agent in this further layer may be the same or different to that in the controlled release layer. Alternatively, the further layer may comprise or consist of no therapeutic agent and one or more disintegrant and one or more wax. Consequently, the further layer may be a delayed release layer. The further layer may be a functional layer, eg a pH sensitive layer (ie the rate of erosion of the layer being dependent on pH), an aesthetic coat (eg, coloured and/or smooth coating).

The therapeutic agents of the present invention may be any element or compound that is useful for the treatment of the animal or human body by enteral administration. The methods of the present invention are however particularly useful for formulating therapeutic agents that benefit from a delayed release, and/or controlled sustained release in the gastrointestinal tract. The person skilled in the art is capable of determining appropriate therapeutic agents, but in the interests of clarity, and not wishing to be restricted further, suitable therapeutic agents may be, metformin hydrochloride, griseofulvin, phenylephrine hydrochloride, opioids, or any combination thereof. Further optional therapeutic agents may be any agent used in methods of therapeutic (including prophylactic) treatment. For example, the therapeutic agent may be any agent for use in the treatment of any one or more of the following: —Central nervous system disorders (e.g. neurogenic pain, stroke, dementia, alzheimer's disease, parkinson's disease, neuronal degeneration, meningitis, spinal cord injury, cerebral vasospasm, amyotrophic lateral sclerosis), cardiovascular disease (e.g. hypertension, atherosclerosis, angina, arterial obstruction, peripheral arterial disease, myocardial pathology, arrhythmia, acute myocardial onfarction, cardiomyopathy, congestive heart failure, coronary artery disease (CAD), carotid artery disease, endocarditis, hypercholesterolemia, hyperlipidemia, peripheral artery disease (PAD), or any combination thereof), Genitourinary disorders (e.g. erectile dysfunction, urinary organ diseases benign prostatic hypertrophy (BPH), renal tubular acidosis, diabetic nephropathy, glomerulonephritis, glomerulosclerosis, urinary tract infection, faecal incontinence, or any combination thereof), ocular disease (e.g. glaucoma, blephartitis, ocular hypertension, retinopathy, conjunctivitis, scleritis, retinitis, keratitis, corneal ulcer, iritis, chorioretinal inflammation, macular edema, xerophthalmia, or any combination thereof), pulmonary disease (e.g. asthma, pulmonary hypertension, acute respiratory distress syndrome, COPD, emphysema, pneumonia, tuberculosis, bronchitis, acute bronchitis, bronchiectasis, bronchiolitis, bronchopulmonary dysplasia, byssinosis, coccidioidomycosis (Cocci), cystic fibrosis, influenza, lung cancer, mesothelioma, or any combination thereof), metabolic diseases (e.g. hypercalciuria, hyperglycemia, hyperinsulinemic hypoglycemia, hyperinsulinism, hyperlysinuria, hypoglycemia or any combination thereof), Exocrine and endocrine diseases (e.g. addison's disease, hypoaldosteronism, cushing's syndrome, diabetes, goitre, hyperthyroidism, hypothyroidism, thyroiditis, pancreatitis or any combination thereof), Hepatic disorders (e.g. hepatitis, non-alcoholic fatty liver disease, cirrhosis, hepatic cancer, primary sclerosing cholangitis, primary biliary cirrhosis, budd-chiari syndrome or any combination thereof), Autoimmune and inflammatory diseases (e.g. multiple sclerosis rheumatoid arthritis, psoriasis, diabetes, sarcoidosis, addison's disease, alopecia areata, amyotrophic lateral sclerosis, ankylosing spondylitis, polyarticular arthritis, atopic allergy, topic dermatitis, autoimmune hepatitis, celiac disease, chagas disease, coeliac disease, cogan syndrome, crohns disease, cushing's syndrome, diabetes mellitus type 1, endometriosis, eosinophilic fasciitis, fibromyalgia/fibromyositis, gastritis, glomerulonephritis, graves' disease. guillain-barré syndrome (GBS), hashimoto's encephalitis, hashimoto's thyroiditis, haemolytic anaemia, idiopathic inflammatory demyelinating diseases, idiopathic pulmonary fibrosis, interstitial cystitis, juvenile idiopathic arthritis, juvenile rheumatoid arthritis, kawasaki's disease, lichen sclerosus, lupus erythematosus, ménière's disease, myasthenia gravis, myositis, narcolepsy, pernicious anaemia, perivenous encephalomyelitis, polymyalgia rheumatica, primary biliary cirrhosis, psoriatic arthritis, reiter's syndrome, rheumatoid fever, sarcoidosis, schizophrenia, sjögren's syndrome, spondyloarthropathy, ulcerative colitis or any combination thereof), Musculoskeletal disorders (e.g. osteoarthritis, osteoporosis, osteonecrosis, arthritis, paget's disease bursitis, costochondritis, tendonitis or any combination thereof), Skin disorders (e.g. acne, alopecia, candidiasis, cellulitis, dermatitis, eczema, epidermolysis bullosa, erythrasma, herpes, erysipelas, folliculitis, impetigo, ringworm, scabies, tinea, trichomycosis or any combination thereof), ENT disorders (e.g. otitis, sinusitis, laryngitis, pharyngitis, laryngitis, meniere's disease, labyrinthitis, or any combination thereof), gastro-intestinal disorders (e.g. irritable bowel syndrome (IBS) necrotizing entercolitis (NEC) non-ulcer dyspepsia, chronic intestinal pseudo-obstruction, functional dyspepsia, colonic pseudo-obstructioduodenogastric reflux, gastroesophageal reflux disease, ileus inflammation, gastroparesis, heartburn, constipation—for exampleconstipation associated with use for medications such as opioids-, colorectal cancer, colonic polyps, diverticulitis, colorectal cancer, barretts esophagus, bleeding in the digestive tract, celiac disease, colon polyps, constipation, crohns disease, cyclic vomiting syndrome, delayed gastric emptying (gastroparesis), diarrhea, diverticulosis, duodenal ulcers, fecal incontinence, gallstones, gas in the digestive tract, gastritis, gastroesophageal reflux disease (GERD), heartburn, hiatal hernia, hemochromatosis, hemorrhoids, hiatal hernia, hirschsprung's disease, indigestion, inguinal hernia, lactose intolerance, peptic ulcers, polyps, *porphyria*, primary biliary cirrhosis, primary sclerosing cholangitis, proctitis, rapid gastric emptying, short bowel syndrome, stomach ulcers, ulcerative colitis, ulcers, whipples disease, or any combination thereof), acute and/or chronic pain, viral infection, cancer, laryngitis, mastoiditis, myringitis, otitis media, rhinitis, sinusitis, sialadenitis, tonsillopharyngitis, or any combination thereof.

Unless indicated to the contrary, all conditions provided herein are measured at a standard temperature and pressure, eg 100 kPa (ie 0.987 atm, 1 bar) and at 20° C.

Unless indicated to the contrary, all amounts of the components of the invention are provided as % by weight of controlled release material.

The skilled person is well aware of what is meant by the term erodible. However, erodible may mean a continuous liberation of compressed material from the surface of the tablet.

Unless indicated to the contrary, where the invention is defined in terms of features selected from a list, or any combination thereof, each combination is contemplated as being disclosed individually herein as a single optional recited feature that may form part of the present invention. Such single optional recited features may be combined with other features of the present invention, unless context excludes this possibility.

The present invention will now be described by way of example and with reference to the FIGURE, in which: —

FIG. 1 shows a magnified image of granules prepared according to the present invention.

1. PRODUCTION OF A DELAYED RELEASE MATERIAL ACCORDING TO THE PRESENT INVENTION

Wax Granules were prepared by melt granulation of the wax glycerol behenate with a disintegrant (i.e. Low-substituted hydroxypropyl cellulose), using one of the methods described below.

1) Laboratory Scale Method <100 g

Glyceryl behenate (i.e. the wax) was melted by heating to 90° C. in a heated water jacketed vessel. Once melted, L-HPC (LH 21 and LH 32) was then gradually added to the molten wax, and resultant mixture combined thoroughly by hand using a spatula. To aid mixing, heat was maintained in the jacketed vessel until a homogenous blend was achieved. Once fully combined the mixture was removed from the heat and granulated by stirring to break up the mixture as it cooled if necessary.

The resultant granules were then milled while warm through a 1.00 mm sieve by hand.

2) Large Scale Hot Melt Extruder Method >5 Kg Scale

Glyceryl behenate and the L-HPC (LH 21 and LH 32) were pre blended using a tumbling motion for a sufficent time to ensure a homogenous mix was obtained. This powder blend was then run through a heated twin screw extruder with temperature raising up to 140° C. with no die plate fitted. The extrudate fell directly into an oscillating granulator running at 120 RPM fitted with a 1.00m mesh screen.

These milled granules from 1 and 2 were then added directly to a heated Caleva spheroniser while the spheronising plate was spinning. The granules were left in the operating spheroniser for the required temperature (typically 60-74° C.), time (typically 0-5 minutes) and speed for small scale spheronisation before being removed and allowed to cool.

The cooled spheronised granules were compressed onto a core tablet to form the delayed release material and so provide a delayed release tablet.

Any core tablet may be used providing it is of an appropriate size for ingestion, e.g. by a human. In this example the following wet granulation process was used to provide an immediate release core tablet.

| API/Excipient | % (w/w) | Location |
|---|---|---|
| Diclofenac potassium | 25 | Intra-granular |
| Microcrystalline cellulose (Avicel ph 101) | 63 | |
| Croscarmellose sodium (AC-DI-SOL) | 1 | |
| Croscarmellose sodium (AC-DI-SOL) | 10 | Extra-granular |
| Magnesium stearate | 1 | |

Weight of water used in granulation process is approximately 72% w/w of final blend weight (or 81% w/w of intragranular blend weight). 100 mg of the core blend is pressed to a hardness of 4-5 kp and a thickness of 3.4 mm±0.17 mm using a 6 mm bi-convex punch and die.

The delayed release layer was put in place using the following protocol. A 10 mm concave punch and die were used to compress the cooled spheronised granules around the core tablet. The required quantity of delayed release spheronised granules were placed onto the lower punch, the core tablet carefully placed on the granule bed and centralised, before placing the remaining granules on top. The contents of the die was then compressed using a single station tablet press.

2, THE EFFECT ON ANGLE OF REPOSE OF WAX GRANULES BEFORE AND AFTER THE SPHERONISATION TECHNIQUE

The milled pre-spheronised granules discussed above in 1. were cooled and their angle of repose determined. The granules were then spheronised and cooled as described above in 1. and under the conditions provided in table 1 belowtheir angle of repose determined.

50 g of the test material was allowed to flow through the orifice of a funnel which was fixed at 5 cm above a flat surface. The magnitude of the angle of the powder heap formed relative to the flat surface was measured and recorded as the angle of repose.

TABLE 1

| Spheronisation Time (mins) | Temperature (° C.) | Speed | Angle of Repose |
|---|---|---|---|
| None | None | None | 39.8° |
| 3 | 72 | Maximum | 30.3° |
| 10 | 74 | 40% | 29.4° |

These results clearly show that the warm spheronisation of the wax granules does significantly improve the flow properties of the granules.

3. EFFECT OF SPHERONISATION ON DELAY TIME BEFORE RELEASE OF ACTIVE

Delayed release tablets formed with the delayed release material processed according to the present invention as a delayed release layer encapsulating a therapeutic core, in accordance with that described in 1. were made. Prior to compression around the core, the granules were spheronised at 72° C. for 3 minutes. A second set of delayed release tablets were prepared in a manner identical to that of the first, but no spheronisation step was carried out.

The period for the delay in the release for both sets of tablets was studied. Dissolution studies were carried out on tablets prepared according to the present invention using an automated ADT8 USP dissolution type II apparatus (TDT08L Bath 1105230, Electrolab Inc., Cupertino, USA), with paddle operated at 50 rpm, at 37° C.±0.5° C. Dissolution was carried out in 900 ml of pH6.8 phosphate buffer. Samples of dissolution media were withdrawn every 5 minutes and the absorbance of the core therapeutic agent was measured by UV analysis using an SP700 High Performance UV Visibility Spectrometer (T70+18-1815-1-0054, PG Instruments Ltd., Wibtoft, U.K.) and compared with a standard prepared to the appropriate concentration. Onset of release was defined as the time at which the absorbance recorded for the therapeutic agent was more than 3%.

Results of the study are shown in Table 2.

| | Spheronised (n = 6 tablets) | Non-Spheronised (n = 6 tablets) |
|---|---|---|
| Delay Time (hr:min) | 03:51 | 02:14 |
| Standard Deviation | 00:21 | 00:12 |
| RSD (%) | 9.3 | 8.9 |

Spheronisation has been demonstrated to have a significant impact on prolongation of release delay, which is thought to be because of its ability to prolong erosion and swelling rate of wax based granules. The methods of the present invention are shown to prolong delay when compacted into tablets.

The invention claimed is:

1. A method for making an erodible controlled release tablet, comprising:
   (a) forming granules comprising 20 to 80% by weight of one or more waxes and 12-50% by weight of one or more disintegrants, wherein the one or more waxes are insoluble in water, and wherein the granules are formed by mixing the one or more disintegrants and the one or more waxes, in molten form, to form a mixture, whilst retaining the one or more waxes in molten form, and solidifying the mixture by cooling below melting point whilst mixing to form the granules;

(b) spheronising the granules; and (c) compacting the spheronised granules around a core tablet comprising an Active Pharmaceutical Ingredient to form a controlled release barrier layer.

2. The method of claim 1, further comprising milling of granules formed in step (a) prior to spheronisation in step (b).

3. The method of claim 1, wherein the one or more waxes are selected from the group consisting of carnauba wax, paraffin wax, castor wax, hydrogenated castor oil, beeswax, glycerol behenate, a glycowax or any combination thereof.

4. The method of claim 1, wherein the one or more disintegrants are selected from the group consisting of LH-11, LH-21, LH-22, LH-32, NBD-021, NBD-020, LH-B1, sodium carboxymethylcellulose, cross-linked starch, hydroxylpropylmethyl cellulose, ion exchange resins or any combination thereof.

5. The method of claim 1, wherein the controlled release barrier layer further comprises a therapeutic agent.

6. A tablet comprising a core and a first layer encapsulating the core, wherein the first layer is an erodible controlled release barrier layer comprising compacted spheronized granules comprising 20 to 80% by weight of one or more waxes and 12-50% by weight of one or more disintegrants; wherein the one or more waxes is insoluble in water; wherein the tablet is formed via the steps comprising:

(a) forming granules comprising 20 to 80% by weight of one or more waxes and 12-50% by weight of one or more disintegrants, wherein the one or more waxes is are insoluble in water, and wherein the granules are formed by mixing the one or more disintegrants and the one or more waxes, in molten form, to form a mixture, whilst retaining the one or more waxes in molten form, and solidifying the mixture by cooling below melting point whilst mixing to form the granules;

(b) spheronising the granules; and (c) compacting the spheronised granules around a core tablet comprising an Active Pharmaceutical Ingredient to form a controlled release barrier layer.

7. The tablet of claim 6, further comprising a second layer encapsulating the first layer.

8. The tablet of claim 7, wherein the second layer comprises one or more therapeutic agents, one or more disintegrants and one or more waxes.

9. The tablet of claim 7, wherein the second layer includes no therapeutic agent.

10. The tablet of claim 7, wherein the second layer is a functional layer.

11. The tablet of claim 6, further comprising one or more therapeutic agents.

* * * * *